United States Patent [19]
Manley

[11] Patent Number: 6,090,817
[45] Date of Patent: Jul. 18, 2000

[54] PHENYLPYRIDINE DERIVATIVES USEFUL AS PHOSPHODIESTERASE INHIBITORS

[75] Inventor: Paul W. Manley, Arlesheim, Switzerland

[73] Assignee: Novartis AG, Basel, Switzerland

[21] Appl. No.: 09/142,099

[22] PCT Filed: Mar. 7, 1997

[86] PCT No.: PCT/EP97/01157

§ 371 Date: Sep. 1, 1998

§ 102(e) Date: Sep. 1, 1998

[87] PCT Pub. No.: WO97/32853

PCT Pub. Date: Sep. 12, 1997

[30] Foreign Application Priority Data

Mar. 8, 1996 [GB] United Kingdom .................... 9604926

[51] Int. Cl.[7] ...................... A61K 31/655; A61K 31/371; A61K 31/41; C07D 413/10; C07D 407/10
[52] U.S. Cl. ...................... 514/277; 546/268.4; 546/118; 546/296; 546/303; 514/359; 514/379; 514/188
[58] Field of Search ..................................... 546/329, 346, 546/280.1, 280.4, 268.1, 290, 268.4, 296, 307, 301, 303, 118; 514/188, 202, 222.2, 226.2, 233.5, 277, 359, 379

[56] References Cited

U.S. PATENT DOCUMENTS 3,329,503  7/1967  Franke et al. .

FOREIGN PATENT DOCUMENTS

| 652 320A | 2/1965 | Belgium . |
|---|---|---|
| 92 06085 | 4/1992 | WIPO . |
| 94 10118 | 5/1994 | WIPO . |
| 96 26921 | 9/1996 | WIPO . |

OTHER PUBLICATIONS

Buu–Hoi et al., "Fluorine–containing analogs of 4–hydroxypropiophenone", Journal of Organic Chemisty, vol. 18, 1953, pp. 910–914.

Buu–Hoi et al., "Orientation in some Friedel–Crafts acylations of 2,2'–dimethyoxybiphenyl, and the cyclization of the reaction products", Journal of Organic Chemistry, vol. 29, 1964. pp. 762–763.

Buu–Hoi et al., "The Pfitzinger reaction with ketones derived from o–hydroxydiphenyl" Journal of Organic Chemistry, vol. 21, 1956, pp. 136–138.

Gray et al., "Mesomorphism and Chemical constitution. Part VIII. The effect of 3'–substituents on the Mesomorphism of the 4'–n–alkoxydiphenyl–4–carboxylic acids and their alkyl esters", Journal of the Chemical Society, 1957, pp. 393–399.

Jin et al., "Wholly aromatic polyesters derived from 6–hydroxy–5–phenyl–2–naphthoic acid and 4'–hydroxy–3'–phenylbiphenyl–4–carboxylic acid", Macromolecular Symposia, vol. 96, 1996, pp. 125–134.

*Primary Examiner*—Alan L. Rotman
*Assistant Examiner*—Rita Desai
*Attorney, Agent, or Firm*—Carol A. Loeschorn

[57] ABSTRACT

(4-oxy-3-(aryl)phenyl)pyridine compounds, in free or acid addition salt form, are useful as pharmaceuticals for treatment and prophylaxis of inflammation, particularly inflammatory or obstructive diseases of the airways, e.g. for asthma therapy. Preferred compounds are novel biphenyl pyridines, biphenyl benzamides and biphenyl phenylcarboxy compounds. The compounds are selective inhibitors of PDE 4 isoenzyme activity and also act to down regulate or inhibit TNF-α release.

18 Claims, No Drawings

PHENYLPYRIDINE DERIVATIVES USEFUL AS PHOSPHODIESTERASE INHIBITORS

This application is a 371 of PCT/EP97/01157 filed Mar. 7, 1997.

The present invention relates to triaryl compounds, particularly biphenyl pyridines, biphenyl benzamides and biphenyl phenylcarboxy compounds, processes for their production., their use as pharmaceuticals and pharmaceutical compositions comprising them.

Specifically, the invention provides a (4-oxy-3-(aryl)phenyl)-azaryl or -arylcarbonyloxy, compound, in free or pharmaceutically acceptable acid addition salt form, for use as a pharmaceutical, e.g. for use in the treatment or prophylaxis of inflammation, particularly inflammatory or obstructive diseases of the airways, e.g. asthma.

In a further embodiment the invention provides a pharmaceutical composition comprising a (4-oxy-3-(aryl)phenyl)-azaryl or -arylcarbonyloxy compound, in free or pharmaceutically acceptable acid addition salt form, e.g. in combination with a pharmaceutically acceptable diluent or carrier.

In a yet further embodiment the invention includes the use of a (4-oxy-3-(aryl)phenyl)-azaryl or -arylcarbonyloxy compound, in free or pharmaceutically acceptable acid addition salt form, for the preparation of a medicament for treatment or prophylaxis of inflammation, particularly inflammatory or obstructive diseases of the airways, e.g. asthma.

In a still yet further embodiment the invention provides a method for treatment or prophylaxis of inflammation, particularly inflammatory or obstructive diseases of the airways, e.g. asthma, comprising administering an effective amount of a (4-oxy-3-(aryl)phenyl)-azaryl or -arylcarbonyloxy compound, in free or pharmaceutically acceptable acid addition salt form, to a subject in need of such therapy.

The (4-oxy-3-(aryl)phenyl)-azaryl or -arylcarbonyloxy compounds of the invention and their pharmaceutically acceptable acid addition salt forms are hereinafter referred to as AGENTS OF THE INVENTION. In these compounds, the 4-oxy moiety is suitably (optionally fluoro-substituted) alkoxy, e.g., (fluoro$_{0-3}$-)C$_{1-4}$alkoxy, e.g. methyl, ethyl, difluoromethyl, or trifluoromethyl. The 3-aryl moiety is suitably a mono- or bicyclic moiety having at least one aromatic ring, e.g., azaryl, for example pyridyl, C$_{1-4}$alkylpyridyl, or quinolinyl; aromatic 2,5-cyclohexadien-3,4-ylidine-1-yl, e.g., benzofurazanyl or benzofuranyl; or phenyl, preferably suitably substituted, e.g., meta- and/or para-substituted, with (i) one or two substitutents selected from nitro, carbamoyl, halo (e.g., chloro), trifluoromethyl, alkoxy (e.g. C$_{1-4}$alkoxy), thioalkoxy (e.g. thio(C$_{1-4}$)alkoxy), alkylsulphoxy (e.g. C$_{1-4}$alkylsulphoxy), alkylsulphonyl (e.g. C$_{1-4}$alkylsulphonyl), cyano, or phenoxy, or (ii) a bridging substituent of 3–5 atoms in length wherein the bridge atoms are selected from C, O, S, and N, e.g. indanyl, benzopyrolidonyl, indanonyl, or benzodioxolanyl. By "azaryl" is meant a nitrogen-containing aromatic group, for example, pyridine, e.g., 3-pyridine or 4-pyridine, quinoline, isoquinoline, imidazopyridine (e.g. imidazo[1,2-a]pyridine or benzamide, e.g., 3- or 4-benzamide. By "arylcarbonyloxy" is meant an aryl moiety, e.g. as defined above for the 3-aryl moiety, bearing at least one carbonyloxy substituent, e.g. in free acid, ester, amide or salt form, preferably a phenylcarboxy moiety, e.g. a phenyl-3- or phenyl-4-carboxy moiety, such as a phenyl carboxylic acid or phenyl carboxylate ester (e.g. lower alkyl phenyl carboxylate ester) or phenylcarboxamido moiety. Halo or halogen as used herein refers to F, Cl, Br or I unless otherwise indicated.

AGENTS OF THE INVENTION include compounds which are known per se but for which no pharmaceutical activity has been described or suggested. Thus Jin et al. (Macromol. Symp. (1995), 96 [International Conference on Liquid Crystal Polymers 1994], 125–134) describe methyl-4'-methoxy-3'-phenylbiphenyl-4-carboxylate and 4'-acetoxy-3'-phenylbiphenyl-4-carboxylic acid as intermediates in the preparation of copolyester liquid crystal materials. Buu-Hoi et al. (J. Org. Chem. 21, [1956], 136–138) describe the preparation of 2-(6-methoxy-biphenyl-3-yl)-quinoline and anolgues thereof further substituted in the quinoline ring by methyl or phenyl at position 3 and/or by carboxy at position 4, and (J. Org. Chem. 29, [1964], 762–763) also describe the preparation of 2-(6,2'-dimethoxy-biphenyl-3-yl)-quinoline and analogues thereof further substituted in the quinoline ring by methyl at position 3 and/or by carboxy at position 4. Buu-Hoi et al. do not identify any utility or activity for these quinoline compounds. Du Pont Belgian patent 652,320 describes the preparation of 5-(6-methoxy-biphenyl-3-yl)-2-methyl thiazole as an intermediate in the preparation 5,5'-diphenylthiazolecarbocyanine sensitisers of silver halide emulsions for photographic use.

Accordingly the present invention provides a (4-oxy-3-(aryl)phenyl)-azaryl or -arylcarbonyloxy compound, e.g. wherein the 4-oxy, 3-aryl, azaryl and arylcarbonyloxy moieties are as defined above, provided
   that the 3-aryl moiety is not unsubstituted phenyl when
      the arylcarbonyloxy moiety is phenyl-4-carboxylic acid or phenyl-4-methylcarboxylate, or
      the azaryl moiety is 5-methylthiazol-2-yl, or
   that the 3-aryl moiety is not unsubstituted phenyl or 2-methoxyphen-1-yl when
      the azaryl moiety is unsubstituted 2-quinoline or 2-quinoline substituted by methyl or phenyl at position 3 and/or by carboxy at position 4,
or a pharmaceutically acceptable acid addition salts thereof.

The novel compounds of this aspect of the invention are encompassed by the AGENTS OF THE INVENTION.

The AGENTS OF THE INVENTION may exist in free form or in the form of pharmaceutically acceptable acid addition salts. Pharmaceutically active acid addition salts for use in the present invention include for example chlorhydrates, oxalates and fumarates.

In particular, the invention provides an AGENT OF THE INVENTION which is a 4-(oxy)-3-[phenyl or (2,5-cyclohexadien-3,4-ylidine-1-yl)]-phenyl-azaryl or -arylcarbonyloxy, in free or pharmaceutically acceptable acid addition salt form. Optionally, the 3-phenyl moiety is substituted, e.g. 3- and/or 4-substituted. The 2,5-cyclohexadien-3,4-ylidine-1-yl moiety is preferably a 2,5-cyclohexadien-3,4-N-ylidine-1-yl moiety, preferably aromatic. Preferably, the oxy moiety is alkoxy, e.g. C$_{1-4}$alkoxy. The azaryl moiety is preferably pyridine, e.g., 4-pyridine, imidazopyridine, e.g. 6-imidazo[1,2-a]pyridine, or benzamide, e.g., 3- or 4-benzamide. Preferably the arylcarbonyloxy moiety is phenylcarboxy, e.g. phenyl-3- or -4-carboxy. For example, the AGENTS OF THE INVENTION include a [2-(C$_{1-4}$alkoxy)-biphenyl-5-yl]pyridine, [2-(C$_{1-4}$alkoxy)-biphenyl-5-yl]benzamide or [2-(C$_{1-4}$alkoxy)-biphenyl-5-yl]phenylcarboxy wherein the biphenyl moiety is optionally 3'- and/or 4'-substituted or optionally 3',4'-fused to a second aromatic ring, preferably a compound of formula Ia or formula Ib:

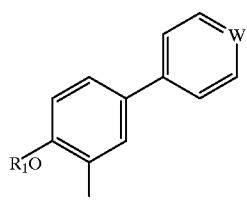

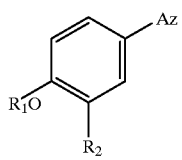

wherein
in formula Ia W is N or C—CO—R,
  wherein R is OH, O—(C$_{1-6}$)alkyl or NR$_3$R$_4$
    wherein R$_3$ and R$_4$ which may be the same or different are H or (C$_{1-6}$)alkyl, or
in formula Ib Az is an azaryl group containing one or more nitrogen atoms, such as quinoline, isoquiniline, indole, imidazopyridine, e.g. imidazo[1,2-a]pyridine, and in both formula Ia and Ib
R$_1$ is (C$_{1-4}$)alkyl, preferably methyl; and
R$_2$ is a phenyl moiety, e.g., of formula II

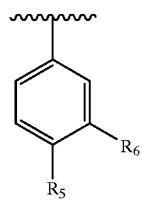

wherein R$_5$ and R$_6$ are, independently, H, nitro, halo (e.g., chloro), trifluoromethyl, (C$_{1-4}$)alkoxy, cyano, or phenoxy; or R$_5$ and R$_6$ together form a bridge of 3–5 atoms in length wherein the bridge atoms are selected from S, O, N, and C, e.g. —OCH$_2$O—, or propylene;
or R$_2$ is a 2,5-cyclohexadien-3,4-ylidine-1-yl moiety, e.g., of formula III

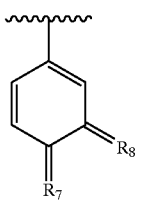

wherein R$_7$ and R$_8$ together form an aromatic bridge of 3–5 atoms in length wherein the bridge atoms are selected from S, O, N, and C, e.g., =N—O—N=;
in free or pharmaceutically acceptable acid addition salt form.

Most preferably, R$_2$ is selected from 3-nitrophenyl, 3-(trifluoromethyl)phenyl, 3-cyanophenyl, 3- or 3,4-halophenyl (e.g., 3-chlorophenyl or 3-chloro-4-fluorophenyl), indan-5-yl, benzofurazan-5-yl, and 1,3-benzo[d]dioxolan-5-yl.

Compounds of formula I thus include:
1. 4-[2-(methoxy)-biphenyl-5-yl]pyridine
2. 4-[2-(methoxy)-3'-(nitro)biphenyl-5-yl]pyridine
3. 4-[2-(methoxy)-3'-(trifluoromethyl)biphenyl-5-yl]pyridine
4. 4-[2-(methoxy)-3',4'-(propylene)biphenyl]pyridine
5. 4-[4(methoxy )-3-(benzofurazan-5-yl)phenyl]pyridine
6. 4-[2-(methoxy)-3'-(cyano)biphenyl-5-yl]pyridine
7. 4-[2-(methoxy)-3'-(chloro)biphenyl-5-yl]pyridine
8. 4-[2-(methoxy)-3',4'-(methylenedioxy)biphenyl-5-yl]pyridine
9. 4-[2-(methoxy)-3'-(phenoxy)biphenyl-5-yl]pyridine
10. 4-[2-(methoxy)-4'-(phenoxy)biphenyl-5-yl]pyridine
11. 4-[2-(Methoxy)-3'-(chloro)-4'-(fluoro)biphenyl-5-yl]pyridine
12. 4'-Methoxy-3'-(benzofurazan-5-yl)-[1,1'-biphenyl]-4-carboxamide
13 4'-Methoxy-3'-(3-nitrophenyl)-[1,1'-biphenyl]-4-carboxylic acid, ethyl ester
14 4'-Methoxy-3'-(3-nitrophenyl)-[1,1'-biphenyl]-3-carboxylic acid, ethyl ester
15 4'-Methoxy-3-methyl-3'-(3-nitrophenyl)-[1,1'-biphenyl]-4-carboxylic acid, ethyl ester
16 3'-(5-Benzofurazanyl)-4'-methoxy-[1,1'-biphenyl]-4-carboxylic acid, ethyl ester
17 3'-(5-Benzofurazanyl)-4'-methoxy-[1,1'-biphenyl]-4-carboxylic acid, 2,2-dimethylpropyl ester
18 3-(5-Benzofurazanyl)-4'-methoxy-[1,1'-biphenyl]-4-carboxylic acid
19 4'-Methoxy-3'-(3-nitrophenyl)-[1,1'-biphenyl]-3-carboxylic acid
20 4'-Methoxy-3-methyl-3'-(3-nitrophenyl)-[1,1'-biphenyl]-4-carboxylic acid
21 3'-(5-Benzofurazanyl )-4'-methoxy-[1,1'-biphenyl]-4-carboxylic acid
22 4-Methoxy-3'-(3-chlorophenyl)-[1,1'-biphenyl]-4-carboxylic acid
23 4'-Methoxy-3'-(3-cyanophenyl)-[1,1'-biphenyl]-4-carboxylic acid
24 4'-Methoxy-3'-(3-nitrophenyl )-[1,1'-biphenyl]-4-carboxamide
25 4'-Methoxy-3'-(3-nitrophenyl)-[1,1'-biphenyl]-3-carboxamide
26 4'-Methoxy-3-methyl-3'-(3-nitrophenyl)-[1,1'-biphenyl]-4-carboxamide
27 N-Methyl-4'-methoxy-3'-(3-nitrophenyl)-[1,1'-biphenyl]-4-carboxamide
28 6-[4-Methoxy-3-(5-benzofurazanyl)phenyl]imidazo[1,2-a]pyridine in free or pharmaceutically acceptable acid addition, e.g., hydrochloride, salt form.

Compounds of formula I are suitably prepared by reacting a compound of formula I'a or formula I'b:

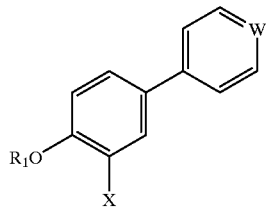

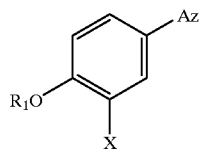

wherein X is halogen(preferably bromine) or a leaving group, such as a tin or boron containing group (preferably —B(OH)₂), and R₁, W and Az are as defined above for formula Ia and Ib, with the desired activated aryl, e.g., aryl halide or aryl boronic acid, for example, a compound of formula IIa or IIIa:

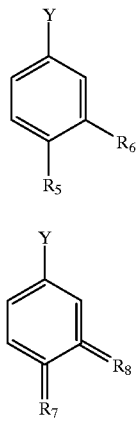

wherein Y is halogen (preferably bromine) or a leaving group, such as a tin or boron containing group (preferably —B(OH)₂), and the R groups are as defined above for Formula II and III; and recovering the resulting compound of the invention, e.g., of formula Ia or Ib, in free or acid addition salt form. Preferably, one of X or Y is halogen, e.g. bromine, and the other is a leaving group, e.g., —B(OH)₂. Suitable reaction conditions may include reaction in the presence of one or more of the following: a nucleophile such as triarylphosphine (preferably tri-o-tolylphosphine or tri-2-furylphosphine); a base such as sodium carbonate, a solvent such as toluene, acetonitrile, or DMF, and/or a suitable catalyst such as a palladium catalyst. Suitable reaction temperatures include from ambient temperature to the boiling point of the solvent, e.g., from 20–150° C., preferably 70–90° C.

Novel intermediates, especially of formula I'a and I'b, are comprised within the scope of the invention. Compounds of formula I'a and I'b can be prepared by a Suzuki- or Stille-type coupling reaction, for example between a 4-alkoxyboronic acid derivative and the suitably substituted haloaromatic system, or alternatively prepared from 4-halopyridine and the corresponding Grignard reagent e.g., by reacting 4-bromopyridine with a compound of formula R₁O—C₆H₄—MgBr wherein R₁ is as defined above, in the presence of a suitable catalyst, e.g., a nickel catalyst, to obtain the 4-aryl-pyridine, which is then halogenated, e.g. by reaction with Br₂, to obtain the compound of formula I'a or I'b where X is halogen, and optionally further reacting with one or more alkylmetal reagents, e.g., with alkyllithium, e.g., butyllithium, followed by reaction with alkylborate, e.g., triethylborate, to obtain the compound of formula I'a or I'b where X is —B(OH)₂. Compounds of formula IIa or IIIa can be prepared analogously, by halogenation of the aryl, e.g., bromination, optionally followed by exchange of the halogen for a leaving group, e.g., —B(OH)₂.

EXAMPLES

Example 1

4-[2-(Methoxy)biphenyl-5-yl]pyridine a) 4-(4-Methoxyphenyl)pyridine

A solution of 4-methoxyphenylmagnesium bromide, prepared from 4-bromoanisole (150 g 0.80 mol) and magnesium (20 g, 0.83 mol) in dry tetrahydrofuran (300 mL) is filtered, cooled to −10° C. and added cautiously to a stirred mixture of bis-(triphenylphosphine)nickel (II) chloride (1.5 g, 2.25 mmol) and 4-bromopyridine hydrochloride (65 g, 0.334 mol) in dry tetrahydrofuran (300 mL) at 10° C. under an argon atmosphere. After 50% of the Grignard reagent had been added a vigorous, exothermic reaction sets in and the temperature of the mixture is maintained between 50 and 60° C. throughout the rest of the addition by employing an ice-methanol cooling bath. When the addition is complete the mixture is stirred for 60 min at 50° C. The solvent is evaporated off under reduced pressure to yield a residue which is treated with t-butylmethylether (500 mL) and extracted with hydrochloric acid (3×300 mL of 5M). The combined extracts are washed (t-butylmethylether), basified (aqueous NaOH) and extracted with t-butylmethylether (4×300 mL). The combined extracts are dried (Na₂SO₄) and the solvent is evaporated off under reduced pressure to yield the crude product which is purified by recrystallisation from t-butylmethylether-cyclohexane to give 4-(4-methoxyphenyl)pyridine as a colourless crystalline solid, m.p. 94–96° C.

b) 4-(3-bromo-4-methoxyphenyl)pyridine

Bromine (26.0 g, 163 mmol) is added to a stirred solution of 4-(4-methoxyphenyl)pyridine (13.6 g, 73.5 mmol) in acetic acid (500 mL) and heated at 60° C. for 72 h. The mixture is then evaporated to dryness under reduced pressure and the residue is treated with aqueous ammonia (400 mL of 6M) and extracted with ethyl acetate (3×200 mL). The combined extracts are dried (Na₂SO₄), filtered and the solvent is evaporated off under reduced pressure to yield the crude product which is purified by chromatography (silica gel, 95% t-butylmethyl ether/4.5% methanol/0.5% aqueous NH₃(25%)) and recrystallised from ether-cyclohexane to give 4-(3-bromo-4-methoxyphenyl)pyridine as a pale-yellow crystalline solid, m.p. 82–84° C.

c) 4-[2-(Methoxy)biphenyl-5-yl]pyridine

A stirred mixture of 4-(3-bromo-4-methoxyphenyl) pyridine (1.32 g, 5 mmol), phenylboronic acid (0.67 g, 5.5 mmol), tri-o-tolylphosphine (0.152 g, 0.50 mmol), palladium (11) acetate (0.056 g, 0.25 mmol), sodium carbonate (1.06 g, 10 mmol) and water (10 mL) in dimethylformamide (20 mL) is heated at 80° C. for 3 h. The mixture is then treated with water (100 mL) and extracted with ethyl acetate (3×80 mL). The combined extracts are washed (saturated NaCl), dried (Na₂SO₄), filtered and the solvent is evaporated off under reduced pressure to yield the crude product which is purified by chromatography (silica gel, 98% ethyl acetate/ 1.8% ethanol/0.2% aqueous NH₃(25%)) to give 4-[4-methoxy-3-(phenyl)phenyl]pyridine base. The base is dissolved in diethylether (5 mL), treated with methanolic HCl (excess), evaporated to dryness under reduced pressure and recrystallised from isopropanol-diethylether to give 4-[2-methoxy-(1,1-biphenyl)-5-yl]pyridine, hydrochloride as a pale-yellow crystalline solid, m.p. 180–200° C., and having the following physical characteristics:

¹H-NMR (δ DMSO-d₆): 3.89 (s, 3H), 7.35 (d, J=8.7 Hz, 1H), 7.39 (d, J=7.2 Hz, 1H), 7.45 (dd, J=7.1 Hz, J=7.2 Hz, 2H), 7.58 (d, J=7.1 Hz, 2H), 7.95 (d, J=2.3 Hz, 1H), 8.08 (dd, J=8.7 Hz, J=2.3 Hz, 1H), 8.2 (broad s, 1H), 8.36 (d, J=6.0 Hz, 2H) and 8.83 (d, J=6.0 Hz, 2H).

Example 2

4-[2-(methoxy)-3'-(nitro)biphenyl-5-yl]pyridine

This compound is prepared analogously to example 1 using 3-(nitro)phenylboronic acid in place of phenylboronic acid to yield the title compound, m.p. 145–150° C.

Example 3

4-[2-(methoxy)-3'-(trifluoromethyl)biphenyl-5-yl] pyridine

This compound is prepared analogously to example 1 using 3-(trifluoromethyl)phenylboronic acid in place of phenylboronic acid to obtain the title compound as the hydrochloride, m.p. 103–106° C.

Example 4

4-[2-(Methoxy)-3',4'-(propylene)biphenyl]pyridine
a) Indan-5-boronic acid

A solution of n-butyllithium in hexane (13.2 mL of 1.6 M, 21 mmol) is added to a stirred solution of 5-bromo-indane (1.06 g, 4 mmol) in dry tetrahydrofuran (30 mL) at −75° C. under an argon atmosphere. The mixture is stirred for 30 min at −65° C., then treated with triethylborate (3.07 g, 21 mmol) and stirred for 60 min at −50° C. The resulting mixture is allowed to warm to 0° C. and then treated with a saturated aqueous solution of ammonium chloride (60 mL) and extracted with ethyl acetate (2×80 mL). The combined extracts are dried (Na₂SO₄), filtered and the solvent is evaporated off under reduced pressure to yield the crude product which is purified by chromatography (silica gel, 50% ethyl acetate in hexaen) and recrystallised from ethyl acetate-hexane to give indan-5-boronic acid as a colourless crystalline solid.
b) 4-[2-(Methoxy)-3',4'-(propylene)biphenyl]pyridine Utilising the procedure described in Example 1 c), but employing indan-5-boronic acid in lieu of phenylboronic acid yielded a crude product which is purified by chromatography (silica gel, 98% ethyl acetate/1.8% ethanol/0.2% aqueous NH₃(25%)) to give 4-[2-(methoxy)-3',4'-(propylene)biphenyl]pyridine base. The base is dissolved in acetone (5 mL), treated with methanolic HCl (excess), evaporated to dryness under reduced pressure and recrystallised from isopropanol-ether to give 4-[2-(methoxy)-3',4'-(propylene)biphenyl]pyridine, hydrochloride as a pale-yellow crystalline solid, m.p. 185–205° C., and having the following physical characteristics:

¹H-NMR (δ DMSO-d₆): 2.06 (m, 2H), 2.91 (m, 4H), 3.07 (s, 3H), 7.27–7.32 (m, 2H), 7.33 (d, J=8.7 Hz, 1H), 7.41 (s, 1H), 7.93 (d, J=2.5 Hz, 1H), 8.07 (dd, J=8.7 Hz, J=2.5 Hz, 1H), 8.42 (d, J=6.0 Hz, 2H) and 8.86 (d, J=6.0 Hz, 2H).

Example 5

4-[4-Methoxy-3-(5-benzofurazanyl)phenyl]pyridine
a) (5-benzofurazanyl)boronic acid Utilising the procedure described in Example 4a), but employing 5-bromobenzofurazan in lieu of 5-bromo-indane yielded a crude product which is purified by recrystallisation from ethyl acetate-hexane to give (5-benzofurazanyl) boronic acid as a beige crystalline solid, m.p. >300° C., and having the following physical characteristics:

¹H-NMR (δ DMSO-d₆+D₂O): 3.66 (s, 3H), 7.84 (d, J=9.1 Hz, 1H), 7.95 (d, J=9.1 Hz, 1H), and 8.37 (s, 1H).
b) 4-[4-Methoxy-3-(5-benzofurazanyl)phenyl]pyridine Utilising the procedure described in Example 1 c), but employing 4-(5-benzofurazanyl)phenylboronic acid in lieu of phenylboronic acid yielded a crude product which is purified by chromatography (silica gel, 98% ethyl acetate/ 1.8% ethanol/0.2% aqueous NH₃(25%)) and recrystallised from ethyl acetate-hexane to give 4-[4-Methoxy-3-(5-benzofurazanyl)phenyl]pyridine as a beige crystalline solid, m.p. 187–192° C.

Example 6

4-[2-Methoxy-3'-cyano-(1,1'-biphenyl)-5-yl]pyridine
a) 2-Methoxy-5-(4-pyridinyl)phenylboronic acid A solution of n-butyllithium in hexane (1.7 mL of 2.5 M, 4.25 mmol) is added to a stirred solution of 4-(3-bromo-4-methoxyphenyl)pyridine (Example 1 b; 1.06 g, 4 mmol) and triethylborate (0.62 g, 4.2 mmol) in dry tetrahydrofuran (20 mL) at −85° C. under an argon atmosphere. The mixture is stirred for 15 min at −80° C., then treated with a saturated aqueous solution of ammonium chloride (60 mL) and extracted with ethyl acetate (2×80 mL). The combined extracts are dried (Na₂SO₄), filtered and the solvent is evaporated off under reduced pressure to yield the crude product which is purified by recrystallisation from ethyl acetate-hexane to give 2-methoxy-5-(pyridin-4-yl) phenylboronic acid as a beige crystalline solid. m.p. 194–200° C. and having the following physical characteristics:

¹H-NMR (δ DMSO-d₆): 3.88 (s, 3H), 7.13 (d, J=8.7 Hz, 1H), 7.68 (d, J=6.1 Hz, 2H), 7.88 (s, 1H), 7.85 (dd, J=8.7 Hz, J=2.4 Hz, 1H), 7.97 (d, J=2.4 Hz, 1H) and 8.60 (d, J=6.1 Hz, 2H).
b) 4-[2-(Methoxy)-3'-(cyano)biphenyl-5-yl]pyridine A stirred mixture of 3-bromobenzonitrile (0.91 g, 5.0 mmol), 2-Methoxy-5-(pyridin-4-yl)phenylboronic acid (0.50 g, 2.3 mmol), tri-o-tolylphosphine (0.152 g, 0.50 mmol), palladium (II) acetate (0.056 g, 0.25 mmol), sodium carbonate (1.59 g, 15 mmol) and water (15 mL) in dimethylformamide (46 mL) is heated at 80° C. for 5 h. The mixture is then treated with water (100 mL) and extracted with ethyl acetate (3×80 mL). The combined extracts are dried (Na₂SO₄). filtered and the solvent is evaporated off under reduced pressure to yield the crude product which is purified by chromatography (silica gel, ethyl acetate) to give 4-[4-methoxy-3-(phenyl)phenyl]pyridine base. The base is dissolved in diethylether (5 mL), treated with methanolic HCl (excess), evaporated to dryness under reduced pressure and recrystallised from ethanol-ether to give 4-[2-methoxy-3'-cyano-biphenyl-5-yl]pyridine, hydrochloride as a pale-yellow crystalline solid, m.p. 142–150° C.

The following compounds are prepared analogously by utilising the appropriate aryl bromides:

Example 7

4-[2-(Methoxy)-3'-(chloro)biphenyl-5-yl]pyridine, hydrochloride, m.p. 156–210° C.

Example 8

4-[2-(Methoxy)-3',4'-(methylenedioxy)biphenyl-5-yl]pyridine, m.p. 168–171° C.

Example 9

4-[2-(Methoxy)-3'-(phenoxy)biphenyl-5-yl]pyridine, hydrochloride, m.p. 184–204° C.

Example 10

4-[2-(Methoxy)-4'-(phenoxy)biphenyl-5-yl]pyridine, hydrochloride, m.p. 173–218° C.

Example 11

4-[2-(Methoxy)-3'-(chloro)-4'-(fluoro)biphenyl-5-yl]
pyridine, hydrochloride, m.p. 115°.

Compounds of Formula I having benzamide or phenylcarboxy in lieu of pyridyl are prepared analogously.

Example 12

4'-Methoxy-3'-(benzofurazan-5-yl)-[1,1'-biphenyl]-4-carboxamide a) 4'-Methoxy-[1,1'-biphenyl]-4-carboxylic acid, ethyl ester A stirred mixture of 4-bromobenzoic acid, ethyl ester (23.6 g, 103 mmol), 4-methoxyphenylboronic acid (15.6 g, 103 mmol), tetrakis(triphenylphosphine)palladium (0) (2.0 g, 1.73 mmol) and powdered caesium fluoride (30.0 g, 200 mmol) in 1,2-dimethoxyethane (300 mL) is heated at 85° C. for 3 h. The mixture is then treated with water (500 mL) and extracted with ethyl acetate (3×100 mL). The combined extracts are washed (saturated NaCl), dried ($Na_2SO_4$), filtered and the solvent is evaporated off under reduced pressure to yield the crude product which is purified by chromatography (silica gel, 5% ethyl acetate/95% cyclohexane) to 4'-methoxy-[1,1'-biphenyl]-4-carboxylic acid, ethyl ester as a colourless crystalline solid. m.p. 103–104° C.

The following compounds are prepared analogously by utilising the appropriate bromobenzoic acid esters and aryl boronic acids:
4'-Methoxy-[1,1'-biphenyl]-3-carboxylic acid, ethyl ester.
4'-Methoxy-3-methyl-[1,1'-biphenyl]-3-carboxylic acid, ethyl ester.

b) 3'-Bromo-4'-methoxy-[1,1'-biphenyl]-4-carboxylic acid, ethyl ester

A solution of bromine (14.6 g, 91.3 mmol) in carbon tetrachloride (100 mL) is added to a stirred mixture of 4'-Methoxy-[1,1'-biphenyl]-4-carboxylic acid, ethyl ester (23.4 g, 91.3 mmol) and silica gal (100 g of particle size 0.040–0.063 mm; Merck 1.09385) in carbon tetrachloride (350 mL). The mixture is stirred at 20° C. for 4 h after which the silica gel is removed by filtration. The filtrate is washed with aqueous sodium hydrogen carbonate (200 mL of 1 M) followed by aqueous sodium thiosulphate (50 mL of 2 M), dried ($Na_2SO_4$), filtered and evaporated to dryness under reduced pressure to give the crude product which is recrystallised from ether-cyclohexane to give 3'-bromo-4'-methoxy-[1,1'-biphenyl]-4-carboxylic acid, ethyl ester as a colourless crystalline solid, m.p. 114–115° C.

The following compounds are prepared analogously by utilising the appropriate esters:
3'-Bromo-4'-methoxy-[1,1'-biphenyl]-3-carboxylic acid, ethyl ester, m.p. 88–90° C.
3'-Bromo-4 '-methoxy-3-methyl-[1,1'-biphenyl]-4-carboxylic acid, ethyl ester, m.p. 84–87° C.

c) 3'-Bromo-4'-methoxy-[1,1'-biphenyl]-4-carboxylic acid

A stirred mixture of 3'-bromo-4'-methoxy-[1,1'-biphenyl]-4-carboxylic acid, ethyl ester (28.8 g, 86 mmol) and aqueous sodium hydroxide (35 mL of 2 M) in ethanol (690 mL) is heated at 90° C. for 2 h. The cooled mixture is then acidified with hydrochloric acid (200 mL of 1.0 M) and the resulting precipitate is filtered off and dried to give 3'-bromo-4'-methoxy-[1,1'-biphenyl]-4-carboxylic acid as a colourless crystalline solid.

d) 3'-Bromo-4'-methoxy-[1,1'-biphenyl]-4-carboxylic acid, 2,2-dimethylpropyl ester A stirred mixture of 3'-bromo-4'-methoxy-[1,1'-biphenyl]-4-carboxylic acid (19.2 g, 62.5 mmol) and dimethylformamide (0.1 mL) in toluene (200 mL) at 20° C. is treated with oxalyl chloride (11.0 mL, 126 mmol).The mixture is then heated at 50° C. for 1 h and then evaporated to dryness under reduced pressure. The resulting crude acid chloride is dissolved in dry tetrahydrofuran (250 mL) and added dropwise to a stirred solution of lithium tert-butylate in tetrahydrofuran (prepared by the slow addition of 32.5 mL of n-butyl lithium to a solution of 23.5 mL of dry t-butanol in 200 mL of dry tetrahydrofuran at 20° C.). The mixture is stirred for an additional 2 h, then treated with a saturated aqueous solution of ammonium chloride (400 mL) and extracted with t-butylethyl ether (2×300 mL). The combined extracts are dried ($Na_2SO_4$), filtered and the solvent is evaporated off under reduced pressure to yield the crude product which is purified by chromatography (silica gel, 20% ethyl acetate in cyclohexane) and recrystallised from t-butylethyl ether-hexane to give 3'-bromo-4'-methoxy-[1, 1'-biphenyl]-4-carboxylic acid, 2,2-dimethylpropyl ester as a colourless crystalline solid.

e) 4-(3-bromo-4-methoxyphenyl)benzamide

Utilizing the procedure of example 1b), but employing 4-(4-methoxyphenyl)benzamide in lieu of 4-(4-methoxyphenyl)pyridine yields 4-(3-bromo-4-methoxyphenyl)benzamide as a beige crystalline solid, m.p. 246–250° C.

f) 4'-Methoxy-3'-(benzofurazan-5-yl )-[1,1'-biphenyl]-4-carboxamide

Utilizing the procedure of example 5b), but employing 4-(3-bromo-4-methoxyphenyl)benzamide in lieu of 4-(3-Bromo-4-methoxyphenyl)pyridine yields a crude product which is purified by chromatography (silica gel, ethyl acetate) and recrystallized from ethanol-ethyl acetate to give the title compound as a beige crystalline solid, m.p. 235–255° C.

Example 13

4-Methoxy-3'-(3-nitrophenyl)-[1,1'-biphenyl]-4-carboxylic acid, ethyl ester

A stirred mixture of 3'-bromo-4'-methoxy-[1,1'-biphenyl]-4-carboxylic acid, ethyl ester (26.6 g, 79.3 mmol), 3-nitrophenylboronic acid (21.2 g, 127 mmol), tri-o-tolylphosphine (2.51 g, 8.26 mmol), palladium (II) acetate (0.91 g, 4.05 mmol), potassium carbonate (21.9 g, 159 mmol) and water (100 mL) in dimethylformamide (400 mL) is heated at 60° C. for 2 h. The mixture is then treated with water (1000 mL) and extracted with ethyl acetate (3×200 mL). The combined extracts are dried ($Na_2SO_4$), filtered and the solvent is evaporated off under reduced pressure to yield the crude product which is purified by chromatography (silica gel, 10% ethyl acetate in cyclohexane) to give 4'-methoxy-3'-(3-nitrophenyl)-[1,1'-biphenyl]-4-carboxylic acid, ethyl ester as a colourless crystalline solid, m.p. 106–108° C.

The following compounds are prepared analogously by utilising the appropriate bromobenzoic acid esters and aryl boronic acids:

Example 14

4'-Methoxy-3'-(3-nitrophenyl)-[1,1'-biphenyl]-3-carboxylic acid, ethyl ester m.p. 87–89° C.

Example 15

4'-Methoxy-3-methyl-3'-(3-nitrophenyl)-[1,1'-biphenyl]-4-carboxylic acid, ethyl ester m.p. 88–90° C.

Example 16

3'-(5-Benzofurazanyl)-4'-methoxy-[1,1'-biphenyl]-4-carboxylic acid, ethyl ester m.p. 166–168° C.

Example 17

3'-(5-Benzofurazanyl)-4'-methoxy-[1,1'-biphenyl]-4-carboxylic acid, 2,2-dimethylpropyl ester m.p. 131–136° C.

Example 18

3'-(5-Benzofurazanyl)-4'-methoxy-[1,1'-biphenyl]-4-carboxylic acid

A stirred mixture of 4'-methoxy-3'-(3-nitrophenyl)-[1,1'-biphenyl]-4-carboxylic acid, ethyl ester (1.88 g, 5 mmol) and aqueous sodium hydroxide (20 mL of 2 M) in ethanol (30 mL) is heated at 90° C. for 3 h. The cooled mixture was then acidified with hydrochloric acid (100 mL of 1.0 M) and the resulting precipitate is filtered off and dried to give 4'-methoxy-3'-(3-nitrophenyl)-[1,1'-biphenyl]-4-carboxylic acid as a colourless crystalline solid, m.p. 270–274° C.

The following compounds are prepared analogously by utilising the appropriate esters:

Example 19

4'-Methoxy-3'-(3-nitrophenyl)-[1,1'-biphenyl]-3-carboxylic acid m.p. 223–228° C.

Example 20

4'-Methoxy-3-methyl-3'-(3-nitrophenyl)-[1,1'-biphenyl]-4-carboxylic acid m.p. 278–281° C.

Example 21

3'-(5-Benzofurazanyl)-4'-methoxy-[1,1'-biphenyl]-4-carboxylic acid m.p.>300° C.

Example 22

4'-Methoxy-3'-(3-chlorophenyl)-[1,1'-biphenyl]-4-carboxylic acid m.p. 250–252° C.

Example 23

4'-Methoxy-3'-(3-cyanophenyl)-[1,1'-biphenyl]-4-carboxylic acid m.p. 280–285° C.

Example 24

4'-Methoxy-3'-(3-nitrophenyl)-[1,1'-biphenyl]-4-carboxamide

A solution of trimethylaluminium in toluene (10 mL of 2.0 M) is added over 30 minutes to a stirred suspension of ammonium choride (1.07 g, 20 mmol) in toluene (20 mL) at 5° C. under an argon atmosphere. The mixture is stirred at 20° C. for 2 h, treated with a solution of 4'-methoxy-3'-(3-nitrophenyl)-[1,1'-biphenyl]-4-carboxylic acid, ethyl ester (1.65 g, 4.3 mmol) in toluene (40 mL) and stirred at 60° C. for 18 h. The cooled mixture is washed with hydrochloric acid (50 mL of 0.5 M) followed by saturated aqueous sodium chloride (50 mL), dried ($Na_2SO_4$). filtered and the solvent is evaporated off under reduced pressure to yield the crude product which is purified by crystallisation from ethyl acetate-t-butylethyl ether to give 4'-methoxy-3'-(3-nitrophenyl)-[1,1'-biphenyl]-4-carboxamide as a colourless crystalline solid, m.p. 201–205° C.

The following compounds are prepared analogously by utilising the appropriate esters:

Example 25

4'-Methoxy-3'-(3-nitrophenyl)-[1,1'-biphenyl]-3-carboxamide m.p. 118–120° C.

Example 26

4'-Methoxy-3-methyl-3'-(3-nitrophenyl)-[1,1'-biphenyl]-4-carboxamide m.p. 179–184° C.

Example 27

N-Methyl-4'-methoxy-3'-(3-nitrophenyl)-[1,1'-biphenyl]-4-carboxamide

Utilising the procedure described in Example 24, but employing methylamine hydrochloride in lieu of ammonium chloride yields a crude product which is purified by chromatography (silica gel. 50% ethyl acetate in cyclohexane) and recrystallised from tetrahydrofuran-cyclohexane to give N-methyl-4'-methoxy-3'-(3-nitrophenyl)-[1,1'-biphenyl]-4-carboxamide as a pale-yellow crystalline solid, m.p. 171–172° C.

A representative imidazopyridine compound is prepared as follows.

Example 28

6-[4-Methoxy-3-(5-benzofurazanyl)phenyl]imidazo[1,2-a]pyridine a) 5-(2-Hydroxyphenyl)benzofurazan A stirred mixture of 5-bromobenzofurazan (11.94 g, 60 mmol), 2-hydroxyphenylboronic acid (9.10 g, 66 mmol). tri-o-tolylphosphine (1.82 g, 6 mmol), palladium (II) acetate (0.672 g, 3 mmol), potassium carbonate (12.4 g, 90 mmol), and water (90 mL) in dimethylformamide (180 mL) is heated at 80° C. under an argon atmosphere for 30 minutes. The mixture is then treated with water (300 mL) and extracted with ethyl acetate (3×100 mL). The combined extracts are washed (saturated NaCl), dried ($Na_2SO_4$), filtered and the solvent is evaporated off under reduced pressure to yield the crude product which is purified by chromatography (silica gel, 20%–100% ethyl acetate in cyclohexane) and recrystallised from ethyl acetate-hexane to give 5-(2-hydroxyphenyl)benzofurazan as a pale-yellow crystalline solid, m.p. 166–169° C.

b) 5-(3-Bromo-6-hydroxyphenyl)benzofurazan

A stirred mixture of 5-(2-hydroxyphenyl)benzofurazan (11.2 g, 52.8 mmol), and tetrabutylammonium tribromide (25.5 g, 52.8 mmol) in dichoromethane (530 mL) is stirred at 18° C. for 18 h. The solvent is evaporated off under reduced pressure to yield a residue which is treated with water (300 mL) and extracted with ethyl acetate (3×100 mL). The combined extracts are washed (saturated NaCl), dried ($Na_2SO_4$), filtered and the solvent is evaporated off under reduced pressure to yield the crude product which is purified by recrystallisation from ethyl acetate-hexane to give 5-(3-bromo-6-hydroxyphenyl)benzofurazan as a pale-yellow crystalline solid, m.p. 179–181° C.

c) 5-(3-Bromo-6-methoxyphenyl)benzofurazan

A stirred mixture of 5-(3-bromo-6-hydroxyphenyl) benzofurazan (8.70 g, 30 mmol), potassium carbonate (14.42 g, 90 mmol) and methyl iodide (2.83 mL, 45 mmol) in dimethylformamide (100 mL) is stirred at 18° C. for 16 h. The mixture is then treated with water (600 mL) and extracted with ethyl acetate (3×150 mL). The combined extracts are washed (saturated NaCl), dried ($Na_2SO_4$), filtered and the solvent is evaporated off under reduced pressure to yield the crude product which is purified by recrystallisation from t-butylmethyl ether-hexane to give 5-(3-bromo-6-methoxyphenyl)benzofurazan as a beige crystalline solid, m.p. 135–137° C.

d) 6-(Trimethylstannyl)imidazo[1,2-a]pyridine

A stirred mixture of 6-bromoimidazo[1,2-a]pyridine (2.36 g, 12 mmol), hexamethylditin (5.0 g, 15.3 mmol), triphenylphosphine (496 mg, 1.89 mmol), and bis(dibenzylidineacetone)palladium(0) (270 mg, 0.47 mmol) in toluene (120 mL) is heated at 118° C. under an argon atmosphere for 6 h. The mixture is then treated with aqueous potassium fluoride solution (300 mL of 0.50 M) and extracted toluene (3×50 mL). The combined extracts are dried ($Na_2SO_4$), filtered and the solvent is evaporated off under reduced pressure to yield the crude product which is purified by chromatography (silica gel, 50% ethyl acetate in cyclohexane) to give 6-(trimethylstannyl)imidazo[1,2-a]pyridine as a colourless oil.

e) 6-[4-Methoxy-3-(5-benzofurazanyl)phenyl]imidazo[1,2-a]pyridine

A stirred mixture of 5-(3-bromo-5-methoxyphenyl) benzofurazan (2.44 g, 8 mmol), 6-(trimethylstannyl)imidazo [1,2-a]pyridine (2.2 g, 7.9 mmol), triphenylphosphine (336 mg, 1.28 mmol), and bis(dibenzylidineacetone)palladium(0) (186 mg, 0.32 mmol) in dimethylformamide (60 mL) is heated at 125° C. under an argon atmosphere for 36 h. The solvent is evaporated off under reduced pressure to yield a crude product which is purified by chromatography (silica gel, 95% ethyl acetate/4.5% ethanol/0.5% aqueous NH3 (25%)) and recrystallised from ethyl acetate-t-butylmethyl ether to give 6-[4-methoxy-3-(5-benzofurazanyl)phenyl] imidazo[1,2-a]pyridine as a pale-yellow crystalline solid, m.p. 190–196° C.

The AGENTS OF THE INVENTION as defined above, e.g., of formula Ia or Ib, particularly as exemplified, in free or pharmaceutically acceptable acid addition salt form, exhibit pharmacological activity and are useful as pharmaceuticals, e.g. for therapy, in the treatment of diseases and conditions as hereinafter set forth.

In particular AGENTS OF THE INVENTION exhibit cyclic nucleotide phosphodiesterase (PDE) isoenzyme inhibiting activity, selective for type 4 isoenzyme.

AGENTS OF THE INVENTION possess anti-inflammatory, anti-airways hyperreactivity and bronchodilator properties. They further possess immunosuppressive, TNFα secretion inhibitory and other pharmacological activities as may be demonstrated in standard test methods for example as follows:

A. PDE4 inhibition: Recombinant PDE4A, PDE4B, PDE4C and PDE4D isoenzyme inhibition assays.

Cloning and expression: PDE4 cDNA coding for the four isoenzymes, human PDE4A (as described by Sullivan et al. Cell Signal 1994; 6:793–812), rat PDE4B (as described by Colicelli et al., Proc. Natl. Acad. Sci. USA 1989; 86:3599–3903), human PDE4C (as described by Engels et al., FEBS Lett. 1995; 358:305–310), and human PDE4D (as described by Baecker et al., Gene 1994; 138:253–256) is cloned either into an extrachromosomal yeast expression vector (PDE4C, PDE4D) or integrated (PDE4A, PDE4B; single copy) at the pep4 locus of a *Saccharomyces cerevisiae* strain lacking both of the wild-type yeast PDE genes. Yeast strains expressing PDE4 isoenzymes are grown in 11 cultures at 30° C., pelleted and frozen until homogenization.

Homogenization: Pelleted yeast (5 mL) is suspended in 50 mL of buffer (10 mM tris-hydroxymethylaminomethane, 1 mM ethylenediamine-tetraacetic acid, 1 mg/mL each of leupeptin and pepstatin A, 175 mg/mL phenylmethylsulphonyl fluoride, 1 mM dithiothreitol, pH 7.4 with HCl). After centrifugation, 15 g of glass beads (425–600 mm, acid washed, Sigma Chemical Co.) washed with buffer are added to the pellet. To this slurry, 1 mL of buffer and 60 mg of cholamidopropane sulphonic acid are added and the slurry is vigorously agitated for 4 h at 4° C. The yeast cells are disintegrated, as observed microscopically (phase-contrast optics) as dark cells and is >30% (usually 50%). The slurry is transferred to a coarse glass funnel and the homogenate collected by suction and washing of the glass beads with a total of 15 mL buffer. Cell fragments are separated from cytosol by centrifugation (2000× g, 10 min. 4° C.). The pellet is resuspended in 15 mL of buffer and assayed for PDE activity together with the cytosol.

PDE assay: The assay protocol is based upon the two-step method described by Thompson et al. (Adv. Second Messenger Phosphoprotein Res. 1979; 10:69–92), modified for 96-well microtitre plates. Briefly, enzyme is diluted with homogenization buffer (see above) in order to obtain between 10% and 30% total substrate hydrolysis during the assay. To start the reaction. 25 mL of diluted enzyme is added to 25 mL of substrate ([3H]-cAMP, 1.25 mM, 740 Bq) and 75 mL of inhibitor solution (see below). After 30 minutes at 37° C., the reaction is stopped in a hot water bath (65° C., 5 minutes). Plates are cooled on ice and incubated for 10 minutes at 37° C. with 25 mL of 5'-nucleotidase (Snake venom, from oiophaghus hannah, Sigma Chemical Co. 0.1 mg/mL in water). The unreacted substrate is separated from [3H]-adenosine by sequentially adding aliquots (100+50+50 mL, at 5 min intervals) of 30% (v/v) Dowex 1×2 slurry (acetate form) in 0.2% (v/v) acetic acid. The Dowex is pelleted by centrifugation (150× g, 5 min). Aliquots of the supernates are transferred onto 96-well, solid-phase scintillation plates (LumaPlate, Canberra Packard) using an automated pipetting device (Hamilton MicroLab 2200), dried (at least 4 h at 50° C.) and counted (Canberra Packard TopCount).

Inhibitors: Inhibitor stock solutions are prepared in dimethylsulphoxide (DMSO) and diluted with water/DMSO to achieve 7 concentrations selected to cover the range of 30% to 70% inhibition. The concentration of DMSO is kept constant at 50 mL/mL throughout the assay.

Determination of inhibition parameters: The concentration at which half-maximal inhibition occurs (IC50) and the steepness of the dose-response curve (Hill's coefficient) are determined from concentration-inhibition curves by non-linear least-squares fitting to the two-parameter logistic equation. Results are expressed as the negative decimal logarithm of inhibitor concentration at which half-maximal inhibition is observed (IC50) (in mol/L; pIC50). 95% confidence intervals were estimated and expressed as pL and pU (negative decimal logarithms of the lower and upper confidence limits, respectively). Concentrations which cause a visible precipitation in the assay are excluded from the analysis.

In this test method AGENTS OF THE INVENTION predominantly inhibit PDE isoenzymes of type 4 having relatively little effect in relation to types 1, 2, 3 and 7. Within the PDE type 4 isoenzyme group (i.e. PDE types 4 A to D) AGENTS OF THE INVENTION generally exhibit selectivity for inhibition of PDE type 4 D isoenzyme in comparison with the PDE type 4 A, 4B and 4C isoenzymes.

B. Anti-inflammatory activity: Inhibition of eosinophil activation by formyl-MetLeuPhe (fMLP)

Purified human eosinophils ($10^4$/well in 0.2 ml HBSS) are stimulated with fMLP (1 $\mu$M) in the presence of lucigenin (25 $\mu$M). Inhibition of the oxidative burst (measured as changes in chemiluminescence) is determined from dose response curves using the logistic equation.

AGENTS OF THE INVENTION are active in test methods A and B at concentrations of the order of from 0.001 to 5 $\mu$M, generally in the low nM range.

C. Influence on allergen-induced pulmonary eosinophilia

Exposure of Brown Norway rats to inhaled antigen (ovalbumin, OA) evokes pulmonary eosinophilia that is maximal 48 hours later. In addition to eosinophil numbers, the activation status of these cells can be assessed by means of enzymatic activity of the eosinophil granule enzyme eosinophil peroxidase (EPO). In the present experiments, inhibition of pulmonary eosinophil accumulation by the AGENTS OF THE INVENTION is assessed.

Ovalbumin (10 $\mu$g/ml) is mixed (i hour on ice) in a blender with aluminum hydroxide (10 mg/ml) and injected s.c. coincidentally with a B. pertussis vaccine (0.25 ml/rat i.p.) into male Brown Norway rats (ca. 200 g). Injection of OA together with adjuvant is repeated 15 and 21 days later. On day 28, sensitized animals are restrained in plastic tubes and exposed for one hour to an aerosal of OA (3.2 mg/ml) using a nose only exposure system. Animals are killed 48 hours later with phenobarbital (250 mg/kg i.p.). The lungs are ravaged using 3 aliquots (4 ml) of Hank's solution (HBSS×10, 100 ml; EDTA 100 mM, 100 ml; HEPES 1 M, 10 ml; 1 liter water), recovered cells are pooled, smeared air dried and stained to differentiate cell types. Cells are identified and counted under oil immersion (×1,000). A minimum of 500 cells per smear are counted and the total population of each cell type is calculated.

Test substance is administered intratracheally 1 hour prior to and 24 hours after OA challenge.

In untreated animals OA challenge induces increase of all cell types in BAL fluid 24 hours after challenge. Prior administration of AGENTS OF THE INVENTION at dosages of the order of from 0.01 to 10 mg/kg reduces eosinophil count in BAL in a dose dependent manner as compared with untreated controls. Cell counts for other leucocytes (macrophages, neutrophils) are also reduced.

Having regard to their anti-inflammatory activity, their influence on airways hyperreactivity and their profile in relation to PDE isoenzyme inhibition, in particular as selective type IV inhibitors, AGENTS OF THE INVENTION are useful for the treatment, in particular prophylactic treatment, of obstructive or inflammatory airways disease. Thus by continued and regular administration over prolonged periods of time AGENTS OF THE INVENTION are useful in providing advance protection against recurrence of bronchoconstrictor or other symptomatic attack consequential to obstructive or inflammatory airways disease or for the control, amelioration or reversal of basal status of such disease.

Having regard to their bronchodilator activity AGENTS OF THE INVENTION are useful as bronchodilators, e.g. for the treatment of chronic or acute broncho-constriction, e.g. for the symptomatic treatment of obstructive or inflammatory airways disease.

The words "treatment" and "treating" as used throughout the present specification and claims in relation to obstructive or inflammatory airways disease are to be understood accordingly as embracing both prophylactic and symptomatic modes of therapy.

In accordance with the foregoing the present invention further provides

A. A method
  a) for the treatment of airways hyperreactivity,
  b) of effecting bronchodilation or, in particular,
  c) of treating obstructive or inflammatory airways disease,
  in a subject in need thereof, which method comprises administering to said subject an effective amount of an AGENT OF THE INVENTION.

Obstructive or inflammatory airways diseases to which the present invention applies include asthma, pneumoconiosis, chronic obstructive airways or pulmonary disease (COAD or COPD) and adult respiratory distress syndrome (ARDS), as well as exacerbation of airways hyperreactivity consequent to other drug therapy, e.g. aspirin or β-agonist therapy.

The present invention is applicable to the treatment of asthma of whatever type or genesis, including intrinsic and, especially, extrinsic asthma. It is applicable to the treatment of allergic (atopic/IgE-mediated) asthma. It is also applicable to the treatment of non-atopic asthma, including e.g. bronchitic, exercise induced and occupational asthma, asthma induced following bacterial infection and other non-allergic asthmas. It is further applicable to the treatment of wheezy infant syndrome (infant, incipient asthma).

The invention is applicable to the treatment of pneumoconiosis of whatever type or genesis including, for example, aluminosis, anthracosis, asbestosis, chalicosis, ptilosis, siderosis, silicosis, tabacoosis and byssinosis.

The invention is applicable to the treatment of COPD or COAD including chronic bronchitis, pulmonary emphysaema or dyspnea associated therewith.

The invention is also applicable to the treatment of bronchitis of whatever type or genesis including, e.g. acute, arachidic, catarrhal, chronic, croupus or phthinoid bronchitis etc.

Having regard to their activity as selective inhibitors of TNF-α release, AGENTS OF THE INVENTION are also useful for the down-regulation or inhibition of TNF-α release, e.g. for the treatment of diseases or conditions in which TNF-α release is implicated or plays a mediating role, e.g. diseases or conditions having an aetiology involving or comprising morbid, for example undesirable, excessive or unregulated TNF-α release, in particular for the treatment of cachexia or endotoxin shock and in treatment of AIDS [cf. Sharief et al, Mediators of Inflammation, 1 323–338 (1992)].

The method of the invention is applicable to the treatment of cachexia associated with morbid TNF-α release or TNF-α blood-serum levels of whatever origin, including cachexia consequential to, e.g. bacterial, viral or parasitic, infection or to deprivation or deterioration of humoral or other organic, e.g. renal function. It is for example applicable to the treatment of cancerous, malarial and vermal cachexia, cachexia resulting from dysfunction of the pituitary, thyroid or thymus glands as well as uremic cachexia. It is in particular applicable to the treatment of AIDS-related cachexia, i.e. cachexia consequential to or associated with to HIV infection.

The method of the invention is also applicable to the treatment of septic shock, e.g., shock conditions resulting from bacterial infection, for example toxic or endotoxic shock. In this regard it is to be noted that the present invention provides a method for the treatment of septic shock as such as well as of conditions consequential to or symptomatic of septic or shock, for example ARDS (adult respiratory distress syndrome). The method of the invention is also applicable to other severe acute inflammatory conditions, for example severe burns, menengitis, and pneumonia.

The method of the invention is further applicable to the treatment of disease consequential to HIV infection, e.g. AIDS, e.g. to the amelioration or control of the advance of such disease. Having regard to their profile in relation to inhibition of PDE isoenzymes and/or TNFα release inhibition, as well as their immunosuppressive activity, AGENTS OF THE INVENTION are also useful as immunosuppressive agents, e.g. for the treatment of autoimmune diseases, in particular for the treatment of autoimmune diseases in which inflammatory processes are implicated or which have an inflammatory component or aetiology, or as anti-inflammatory agents for the treatment of inflammatory disease in particular for the treatment of inflammatory disease in which autoimmune reactions are implicated or having an autoimmune component or aetiology.

Examples of such disease to which the present invention is applicable include autoimmune hematological disorders (e.g. hemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease) endocrine ophthalmopathy, Grave's disease, sarcoidosis, alveolitis, chronic hypersensitivity pneumonitis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), as well as inflammatory and/or hyperproliferative skin diseases such as psoriasis atopic dermatitis, pemphigus and, in particular, contact dermatitis, e.g. allergic contact dermatitis.

AGENTS OF THE INVENTION are in particular useful for the treatment of arthritis, and other rheumatic or inflammatory disease, especially for the treatment of rheumatoid arthritis.

As immunosuppressants AGENTS OF THE INVENTION are further indicated for use in the prevention of graft rejection, e.g. for the maintenance of allogenic organ transplants or the like, e.g. in relation to kidney, liver, lung, heart, heart-lung, bowel, bone-marrow, skin, or corneal transplant.

Having regard to their anti-inflammatory activity, in particular in relation to inhibition of eosinophil activation, AGENTS OF THE INVENTION are also useful for the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoal) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Having regard to their profile in relation to inhibition of PDE isoenzymes, in particular their profile as selective type IV inhibitors, AGENTS OF THE INVENTION are further useful as type IV PDE inhibitors, for example for the treatment of disease involving tissue calcium depletion, in particular degenerative diseases of the bone and joint involving calcium depletion, especially osteoporosis. In this regard they are further useful for the treatment of allergic inflammatory diseases such as rhinitis, conjunctivitis, atopic dermatitis, urticaria and gastro-intestinal allergies; as vasodilators, e.g. for the treatment of angina, hypertension, congestive heart failure and multi-infarct dementia; and for the treatment of other conditions where inhibition of PDE IV is indicated, for example, depression, conditions and diseases characterized by impaired cognitive function including Alzheimer's disease, Parkinson's disease and stroke.

Having regard to their ability to interact synergistically with immunosuppressive and/or anti-inflammatory drug substances, AGENTS OF THE INVENTION are also useful as co-therapeutic agents for use in conjunction with such drugs, e.g. as potentiators of therapeutic activity of such drugs or as means of reducing required dosaging or potential side effects of such drugs. Drug substances with which AGENTS OF THE INVENTION may suitably be co-administered include, e.g. cyclopeptide, cyclopeptolide or macrolide immunosuppressive or anti-inflammatory drug substances, for examples drugs belonging to the cyclosporin class, e.g. cyclosporins A or G, the drug substances tacrolimus (also known as FK 506), ascomycin and rapamycin and their various known congeners and derivatives, as well as glucocorticosteroid drugs. Diseases to which such co-therapy may be applied include e.g. any disease or condition requiring immunosuppressive or anti-inflammatory drug therapy, e.g. as hereinbefore set forth. In particular AGENTS OF THE INVENTION are suitable for use in co-therapy as aforesaid, e.g. for the purposes of immunosuppressive, anti-inflammatory or anti-asthmatic treatment, e.g. to achieve cyclosporin, e.g. cyclosporin A-, macrolide- or steroid-sparing effect.

In accordance with the foregoing the present invention also provides:

B. A method
  a) for the down-regulation or inhibition of TNF-α release,
  b) for the inhibition of PDE IV isoenzyme activity,
  c) of effecting immunosuppression,
  d) for the treatment of inflammatory disease, or
  e) for the treatment of any particular condition or disease as hereinabove set forth,
  in a subject in need thereof, which method comprises administering to said subject an effective amount of an AGENT OF THE INVENTION.

The present invention also provides:

C. An AGENT OF THE INVENTION for use as a pharmaceutical, for example for use in any method or in the treatment of any disease or condition as hereinbefore set forth, e.g. as defined under A or B above.

Dosages employed in practicing the present invention will of course vary depending, e.g. on the particular disease or condition to be treated, the particular AGENT OF THE INVENTION used, the mode of administration and the therapy desired. In general, however, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered 1× or in divided doses 2 to 4× daily or in sustained release form. Unit dosage forms for oral administration thus suitably comprise from about 0.2 to 75 or 150, e.g. from about 0.2 or 2.0 to 50, 75 or 100 mg AGENT OF THE INVENTION, together with a pharmaceutically acceptable diluent or carrier therefor.

For use in the treatment of chronic or obstructive airways disease, e.g. asthma AGENTS OF THE INVENTION may also be administered by the inhaled route. Again dosages employed will vary, e.g. depending on the particular disease or condition, the particular AGENT OF THE INVENTION employed, the particular mode of administration (e.g. whether by dry powder inhalation or otherwise) and the effect desired. In general, however, an indicated inhaled daily dosage will be of the order of from about 2.5 to about 130.0 $\mu$g/kg/day e.g. from about 13.0 to about 60.0 $\mu$g/kg/day. For larger mammals, for example humans, an indicated daily dosage for administration by inhalation, e.g. in the treatment of asthma, will be in the range of from about 0.2 to about 10.0 mg, e.,. from about 1 to about 5 mg, conveniently given in one single administration or 2 or 3 separate administrations throughout the day. An appropriate dosage per administration will thus be of the order of from about 200 $\mu$g to about 3.3 mg, with administration up to 3 times daily, suitably administered from a dry powder inhalation delivery device in a series of 2 to 8 puffs at each administration.

AGENTS OF THE INVENTION may also be administered by any other appropriate route, e.g. by infusion, for example for the treatment of endotoxin shock; nasally, for example for the treatment of rhinitis; ocularly, for example for the treatment of autoimmune diseases of the eye; dermally, i.e. topically to the skin, for example for the treatment of dermatoses or psoriasis; or rectally, e.g. via enemation or suppository, for example for the treatment of inflammatory bowel disease. Suitable dosages for application by such routes will generally be of the order of 10 to 100× less than those required for oral administration.

Pharmaceutical compositions comprising AGENTS OF THE INVENTION may be prepared using conventional diluents or excipients and techniques known in the galenic art. Thus oral dosage forms may include tablets, capsules and the like. Formulations for dermal administration may take the form of creams, ointments, gels, or transdermal delivery systems, e.g. patches and, in addition to inert diluents or carriers, may suitably contain skin penetration enhancing agents, again as known in the art.

Compositions for inhalation may comprise aerosol or other atomizable formulations as well as inhalable dry powder formulations, with or without diluent, for administration by any appropriate dry powder inhalation system as known in the art. For the preparation of dry powder forms for inhalation, AGENTS OF THE INVENTION are suitably employed in pharmaceutically acceptable acid addition salt form. The said salt form is suitably milled, e.g. using an air-jet or ceramic mill to provide a finely divided inhalable powder, e.g. having an average particle diameter of ca. 2–3$\mu$. Appropriately at least 90% of the material will have an average particle diameter of less than 7.8$\mu$, more preferably of less than 4.8 g. In order to ensure obtention of an appropriate and consistent particulate product suitable for administration by inhalation in dry powder from, it may be preferable to effect milling of the active ingredient premixed with an appropriate inhalable carrier medium, e.g. lactose, under conditions of reduced temperature.

In accordance with the foregoing the present invention also provides: a pharmaceutical composition comprising an agent of the invention together with a pharmaceutically acceptable diluent or carrier therefor, e.g. for use in any method as hereinbefore defined.

What is claimed is:

1. A ((4-oxy-3-(aryl)phenyl)-pyridine compound, in free or pharmaceutically acceptable acid salt form, wherein aryl is phenyl substituted with a bridging substituent of 3–5 atoms in length wherein the bridge atoms are selected form C, O, S and N, or aryl is an aromatic 2,5-cyclohexadien-3,4-ylidene-1-yl moiety of formula III

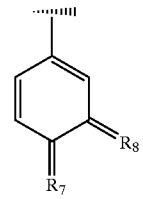

III wherein $R_7$ and $R_8$ together form a hetero atomic bridge of 3–5 atoms in length wherein the bridge atoms are selected from S, O, N and C.

2. A pharmaceutical composition comprising a compound according to claim 1 in combination with a pharmaceutically acceptable diluent or carrier.

3. A compound of formula Ia

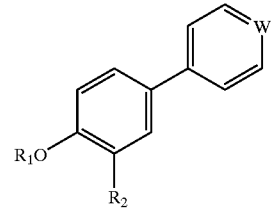

Ia wherein
W is N,
$R_1$ is $C_{1-4}$alkyl and
$R_2$ is a phenyl moiety of formula II

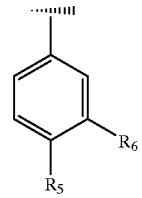

II wherein $R_5$ and $R_6$ together form a hetero bridge of 3–5 atoms in length wherein the bridge atoms are selected from S, O, N, and C;
or $R_2$ is a 2,5-cyclohexadien-3,4-ylidine-1-yl moiety, of formula III

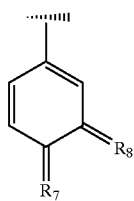

wherein $R_7$ and $R_8$ together form a hetero aromatic bridge of 3–5 atoms in length wherein the bridge atoms are selected from S, O, N, and C;

in free or pharmaceutically acceptable acid addition salt form.

4. A compound according to claim 3, wherein $R_1$ is methyl.

5. A compound according to claim 3, wherein $R_2$ is a phenyl moiety of formula II in which $R_5$ and $R_6$ together denote —$OCH_2O$—.

6. A compound according to claim 4, wherein $R_2$ is a phenyl moiety of formula II in which $R_5$ and $R_6$ together denote —$OCH_2O$—.

7. A compound according to claim 3, wherein $R_2$ is a moiety of formula III in which $R_7$ and $R_8$ together denote =N—O—N=.

8. A compound according to claim 4, wherein $R_2$ is a moiety of formula III in which $R_7$ and $R_8$ together denote =N—O—N=.

9. A compound selected from the group consisting of
4-[4-(methoxy)-3-(benzofurazan-5-yl)phenyl]pyridine, or
4-[2-(methoxy)-3',4'-(methylenedioxy)biphenyl-5-yl] pyridine,
in free or pharmaceutically acceptable acid addition salt form.

10. A method
a) for the down-regulation or inhibition of TNF-α release,
b) for the inhibition of PDE 4 isoenzyme activity,
c) of effecting immunosuppression,
d) for the treatment of inflammatory disease, or
e) treatment of airways hyperreactivity or
f) effecting bronchodilation
in a subject in need thereof, which method comprises administering to said subject an effective amount of a compound according to claim 1.

11. A method according to claim 10, in which the inflammatory disease is an obstructive or inflammatory airways disease.

12. A method according to claim 11, in which the airways disease is asthma.

13. A method
a) for the down-regulation or inhibition of TNF-α release,
b) for the inhibition of PDE 4 isoenzyme activity,
c) of effecting immunosuppression,
d) for the treatment of inflammatory disease, or
e) treatment of airways hyperreactivity or
f) effecting bronchodilation
in a subject in need thereof, which method comprises administering to said subject an effective amount of a compound according to claim 3.

14. A method according to claim 13, in which the inflammatory disease is an obstructive or inflammatory airways disease.

15. A method according to claim 14, in which the airways disease is asthma.

16. A method
a) for the down-regulation or inhibition of TNF-α release,
b) for the inhibition of PDE 4 isoenzyme activity,
c) of effecting immunosuppression,
d) for the treatment of inflammatory disease, or
e) treatment of airways hyperreactivity or
f) effecting bronchodilation
in a subject in need thereof, which method comprises administering to said subject an effective amount of a compound according to claim 9.

17. A method according to claim 16, in which the inflammatory disease is asthma.

18. A process for the preparation of a compound according to claim 1 comprising reacting a compound of formula I'a:

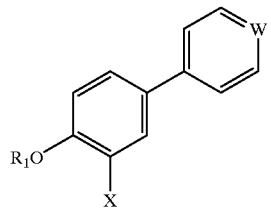

wherein X is halogen or a tin- or boron-containing leaving group;
$R_1$ is $C_{1-4}$alkyl; and
W is N;
with an activated aryl compound of formula IIa or IIIa:

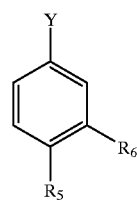

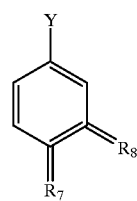

wherein Y is halogen or a tin- or boron-containing leaving group;
$R_5$ and $R_6$ together form a hetero bridge of 3–5 atoms in length wherein the bridge atoms are selected from S, O, N, and C;
$R_7$ and $R_8$ together form a hetero aromatic bridge of 3–5 atoms in length wherein the bridge atoms are selected from S, O, N and C;
and recovering the resulting compound, in free or pharmaceutically acceptable acid addition salt form.

* * * * *